US012746005B2

(12) United States Patent
Ogawa et al.

(10) Patent No.: US 12,746,005 B2
(45) Date of Patent: Sep. 29, 2026

(54) MEDICAL DEVICE WITH BASKET

(71) Applicant: KANEKA CORPORATION, Osaka (JP)

(72) Inventors: Atsushi Ogawa, Tokyo (JP); Masayuki Takatera, Settsu (JP)

(73) Assignee: KANEKA CORPORATION, Osaka (JP)

( * ) Notice: Subject to any disclaimer, the term of this patent is extended or adjusted under 35 U.S.C. 154(b) by 36 days.

(21) Appl. No.: 18/850,435

(22) PCT Filed: Mar. 9, 2023

(86) PCT No.: PCT/JP2023/009150
§ 371 (c)(1),
(2) Date: Sep. 24, 2024

(87) PCT Pub. No.: WO2023/189386
PCT Pub. Date: Oct. 5, 2023

(65) Prior Publication Data

US 2025/0204916 A1 Jun. 26, 2025

(30) Foreign Application Priority Data

Mar. 29, 2022 (JP) ................................ 2022-053544

(51) Int. Cl.
*A61B 17/12* (2006.01)
*A61B 90/00* (2016.01)
*A61B 17/00* (2006.01)

(52) U.S. Cl.
CPC .. *A61B 17/12113* (2013.01); *A61B 17/12172* (2013.01); *A61B 90/39* (2016.02);
(Continued)

(58) Field of Classification Search
CPC .................... A61B 17/12172; A61B 17/12113
See application file for complete search history.

(56) References Cited

U.S. PATENT DOCUMENTS 6,346,117 B1 * 2/2002 Greenhalgh ..... A61B 17/12022
606/200
9,078,658 B2 * 7/2015 Hewitt ............ A61B 17/12013
(Continued)

FOREIGN PATENT DOCUMENTS

JP 2001-518320 A 10/2001
JP 2011-519632 A 7/2011
(Continued)

OTHER PUBLICATIONS

International Search Report (PCT/ISA/210) issued in PCT/JP2023/009150, dated May 23, 2023.

*Primary Examiner* — Erin Mcgrath
(74) *Attorney, Agent, or Firm* — Birch, Stewart, Kolasch & Birch, LLP

(57) ABSTRACT

A medical device comprising: a basket; a connection member disposed on a proximal side with respect to the basket; and a basket pusher disposed on the proximal side with respect to the connection member, wherein the connection member is configured to be bendable such that in a state where, a 0.1 g weight is connected, in 37° C. warm water, on a distal side with respect to a middle point of a length from the distal end of the basket to the proximal end of the basket, an angle on the proximal side between the extending direction of the basket pusher in a state where the basket pusher is horizontally fixed and the straight line passing through the distal end of the basket and the proximal end of the basket is 150 degrees or less.

15 Claims, 4 Drawing Sheets

(52) U.S. Cl.
CPC ............... *A61B 2017/00477* (2013.01); *A61B 2017/00862* (2013.01); *A61B 2017/12068* (2013.01); *A61B 2090/3966* (2016.02)

(56) References Cited

U.S. PATENT DOCUMENTS

| | | | | |
|---|---|---|---|---|
| 2006/0052816 | A1* | 3/2006 | Bates | A61B 17/12022 606/200 |
| 2009/0025820 | A1* | 1/2009 | Adams | A61B 17/12172 140/71 C |
| 2009/0275974 | A1 | 11/2009 | Marchand et al. | |
| 2013/0085520 | A1* | 4/2013 | Liang | A61B 17/12113 606/195 |
| 2013/0245667 | A1 | 9/2013 | Marchand et al. | |
| 2014/0018838 | A1* | 1/2014 | Franano | A61B 17/12136 606/195 |
| 2015/0105817 | A1 | 4/2015 | Marchand et al. | |
| 2015/0150563 | A1 | 6/2015 | Marchand et al. | |
| 2015/0272589 | A1 | 10/2015 | Lorenzo | |
| 2017/0035545 | A1* | 2/2017 | Watanabe | A61F 2/0105 |
| 2017/0224350 | A1 | 8/2017 | Shimizu et al. | |
| 2017/0224355 | A1 | 8/2017 | Bowman et al. | |
| 2018/0000489 | A1 | 1/2018 | Marchand et al. | |
| 2018/0271540 | A1 | 9/2018 | Merritt et al. | |
| 2019/0008522 | A1 | 1/2019 | Lorenzo | |
| 2020/0113576 | A1 | 4/2020 | Gorochow et al. | |
| 2020/0281603 | A1 | 9/2020 | Marchand et al. | |
| 2020/0289125 | A1* | 9/2020 | Dholakia | A61B 17/12172 |
| 2020/0323534 | A1 | 10/2020 | Shimizu et al. | |
| 2021/0169499 | A1 | 6/2021 | Merritt et al. | |
| 2021/0196284 | A1 | 7/2021 | Gorochow et al. | |
| 2021/0228214 | A1 | 7/2021 | Bowman et al. | |
| 2021/0330331 | A1 | 10/2021 | Lorenzo | |
| 2022/0183868 | A1* | 6/2022 | Ichimura | A61M 25/0026 |
| 2023/0270445 | A1 | 8/2023 | Shimizu et al. | |
| 2024/0065701 | A1 | 2/2024 | Merritt et al. | |

FOREIGN PATENT DOCUMENTS

| | | | |
|---|---|---|---|
| JP | 2015-196092 | A | 11/2015 |
| JP | 2019-506230 | A | 3/2019 |
| JP | 2019-193816 | A | 11/2019 |
| JP | 2020-58808 | A | 4/2020 |
| JP | 2020-509922 | A | 4/2020 |
| WO | WO 99/05977 | A1 | 2/1999 |

* cited by examiner

[Fig. 1]
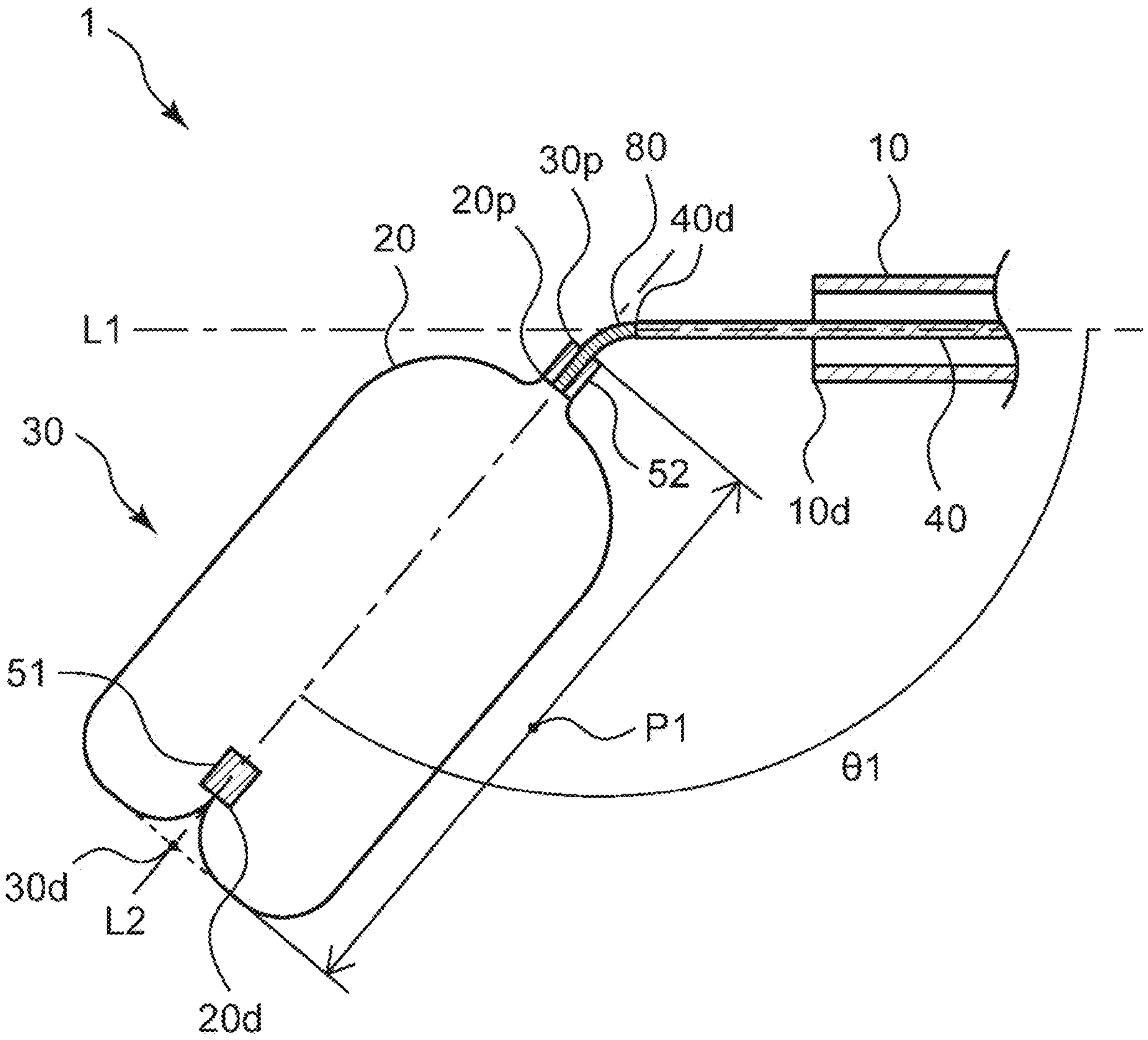

[Fig. 2]
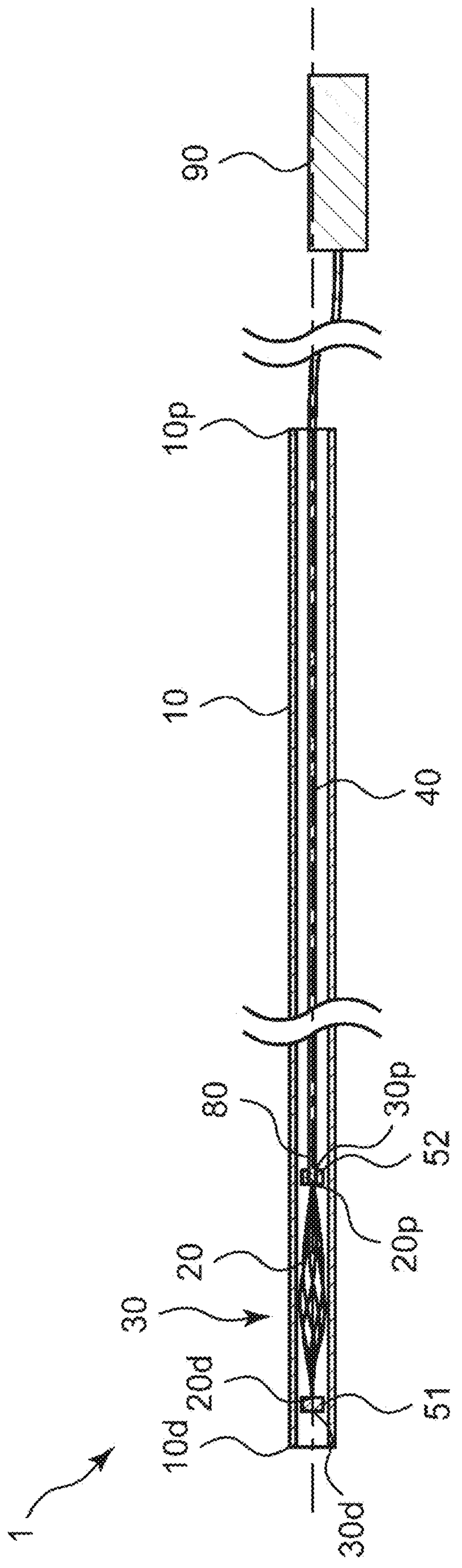

[Fig. 3]
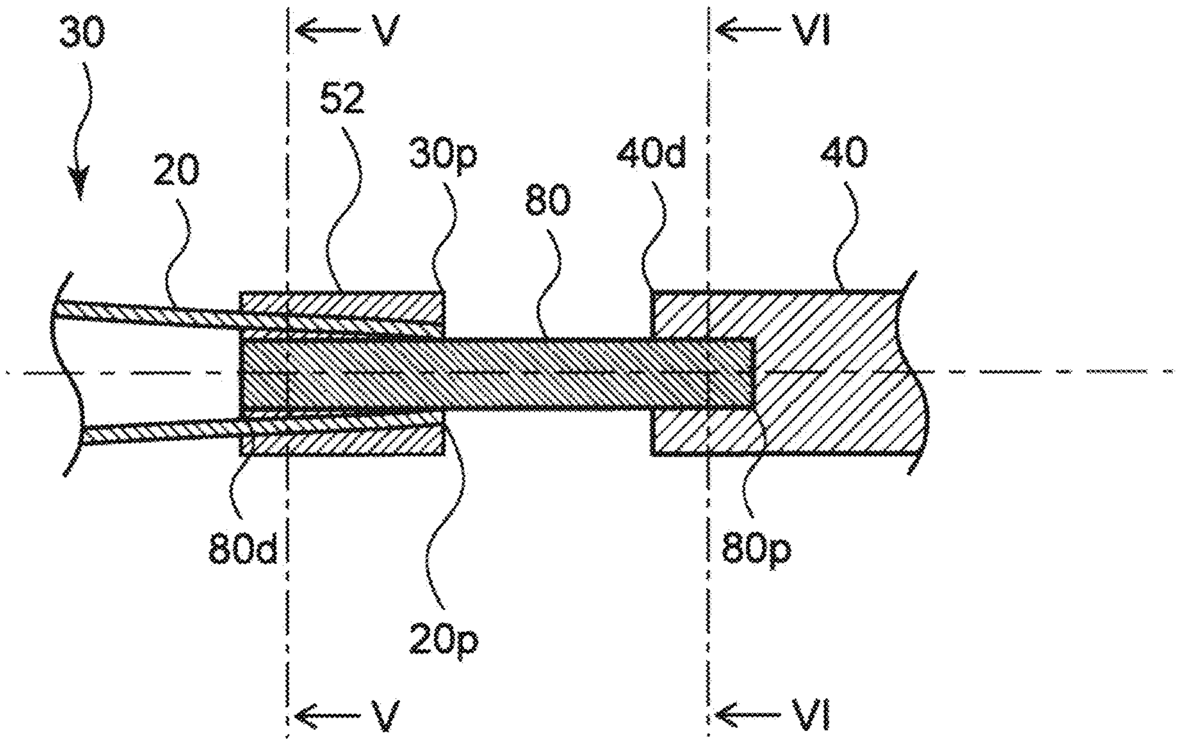
[Fig. 4]
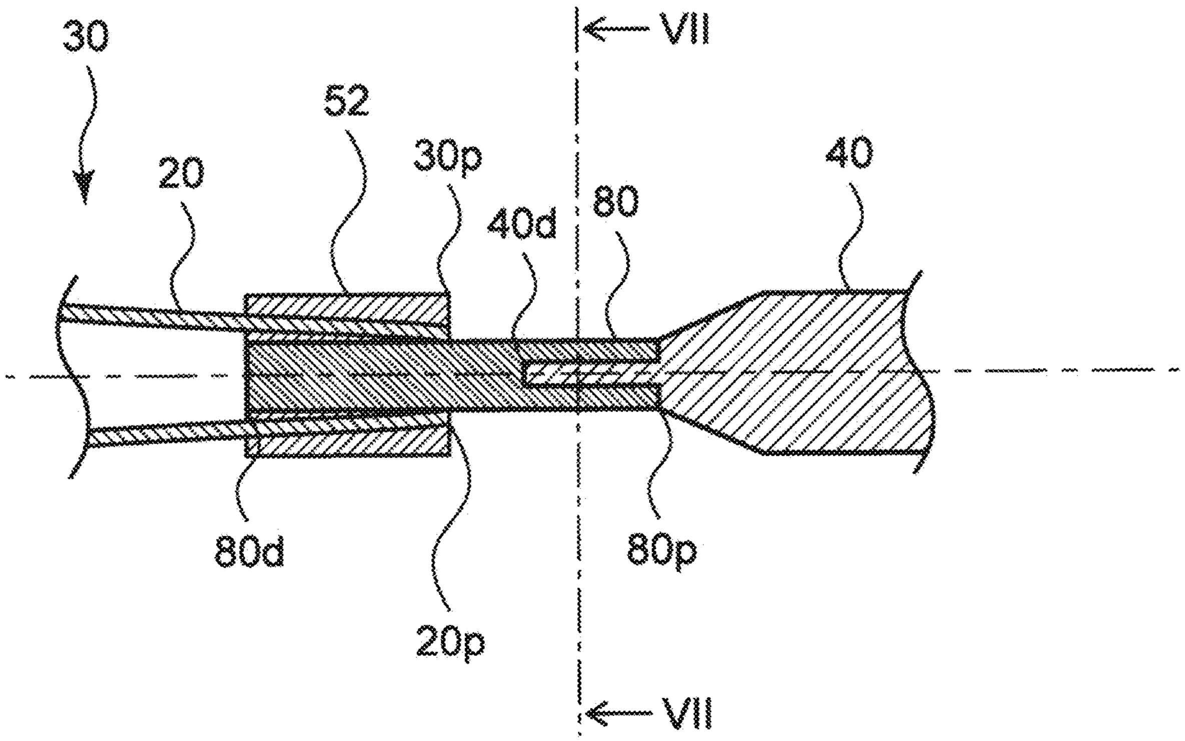

[Fig. 5]
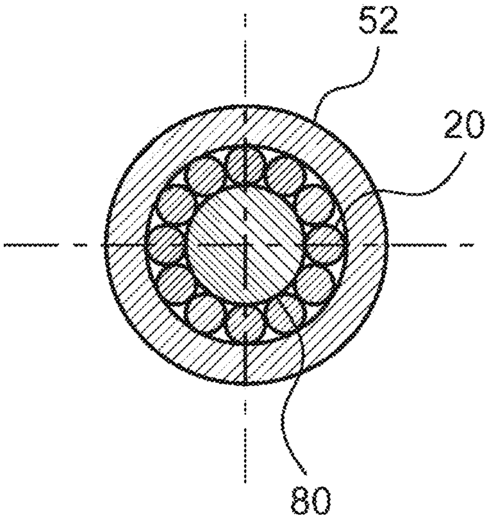
[Fig. 6]
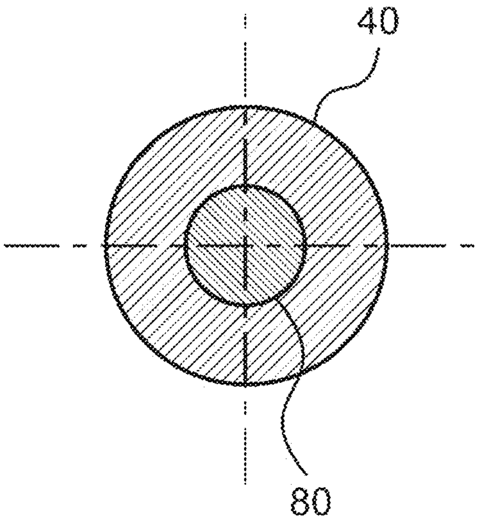
[Fig. 7]
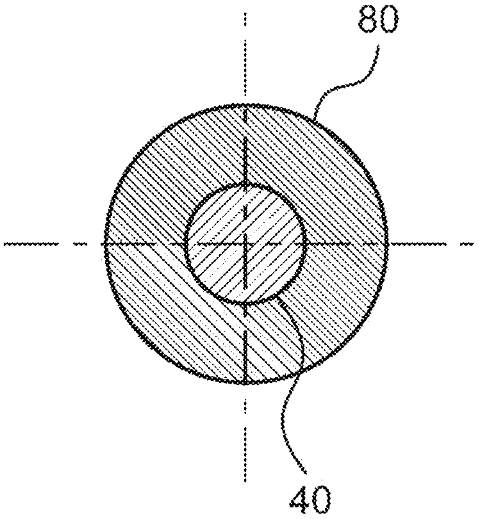

MEDICAL DEVICE WITH BASKET

TECHNICAL FIELD

The present invention relates to a medical device that is used for an in-vivo lumen such as a blood vessel.

BACKGROUND ART

Endovascular treatment is an example of treatment methods for vascular lesions such as aneurysms in the head and neck region, arteriovenous malformations, arteriovenous fistulas, pulmonary vascular malformations, renovascular malformations, renal artery, abdominal aneurysms, and the like. As an endovascular treatment, for example, embolization in which an embolization device having an embolization coil is indwelled at a target site such as the inside of a bulge such as an aneurysm, to promote thrombosis, thereby preventing rupture of the bulge, is used.

When the opening of an aneurysm or the like in a blood vessel wall is large, an embolization coil indwelled inside the bulge may come out of the bulge. In order to prevent the coil indwelled in the bulge from deviating from the bulge, an indwelling device to be disposed in the bulge or a blood vessel near the opening of the bulge may be used. Further, embolization in which a basket is disposed in a bulge, a coil is packed in this basket, and the coil is left in the bulge to fill the bulge, thereby preventing rupture of the bulge, is also known.

For example, Patent Literature 1 describes a device for treating an aneurysm in a parent vessel defining a lumen, the aneurysm having a neck and an inner wall defining an inner cavity in communication with the lumen, the device being configured to be expanded in the inner cavity, the device including a collapsible member adjusted such that, when the device is expanded, the member bridges the neck of the aneurysm and comes into contact with the inner wall. Patent Literature 2 describes a device that includes a self-expandable-type resilient permeable shell. The self-expandable-type resilient permeable shell includes a plurality of elongated resilient filaments with a woven structure fixed to each other at proximal ends and distal ends of the filaments. Further, the self-expandable-type resilient permeable shell has: a radially constrained elongated state configured for delivery within a microcatheter, with the thin woven filaments extending longitudinally from the proximal end to the distal end radially adjacent to each other along the lengths of the filaments; and an expanded relaxed state with a globular longitudinally shortened configuration relative to the radially constrained state, with the woven filaments forming the self-expandable-type resilient permeable shell in a smooth path radially expanded from the longitudinal axis between the proximal end and the distal end including a plurality of openings in the shell formed between the woven filaments. The largest of the openings is configured to allow blood flow through the openings at a velocity below a thrombotic threshold velocity. Patent Literature 3 describes an occlusion device including: a substantially tubular structure that has a proximal end region and a distal end region, that has a first expanded state and a second collapsed state, that has, in the second collapsed state, dimensions suitable for insertion through the vascular system of a patient into the neck of an aneurysm, that has an outer surface capable of coming into contact with the aneurysm in the expanded state, and that further has an inner surface; and a control ring disposed in the proximal end region of the structure and having a substantially annular body at least substantially surrounding the proximal end region in order to prevent expansion in the radial direction of the proximal end region and to provide an engagement feature during operation of the occlusion device. Patent Literature 4 describes an occlusion device including: a holder formed by a plurality of wires braided in a cylindrical shape whose proximal end is closed; and a catheter whose closed proximal end has a first opening and which has a leading end connected so as to be attachable to and detachable from the holder, the catheter having a passage extending to the distal end of the catheter and being aligned with the first opening of the holding part, an embolus material in the passage of the catheter being able to advance through the passage and the first opening into the cylindrical shape of the holding part. Patent Literature 5 describes a device including a self-expanding permeable shell having a proximal end, a distal end, and a longitudinal axis, the shell including a plurality of elongated resilient filaments having a braided structure, the filaments being secured at least one of the proximal end or the distal end of the permeable shell, the permeable shell having a radially constrained elongated state configured for delivery in a microcatheter and having an expanded state with an axially shortened configuration relative to the radially constrained state, the permeable shell having a plurality of openings formed between the braided filaments, the permeable shell in the expanded state thereof including a plurality of circumferentially-arrayed lobes. Patent Literature 6 describes a device including an implant movable from a collapsed state to an expanded state, the implant including a proximal end, a distal end, and a braided segment forming a substantially continuous braided structure between the proximal end and the distal end, wherein in the expanded state, the implant includes: an outer occlusive sack extending from the proximal end of the implant and capable of occluding an aneurysm neck; an inner occlusive sack extending and forming the distal end of the implant and forming a groove in the outer occlusive sack; and a fold part in the braided segment positioned between the outer occlusive sack and the inner occlusive sack.

CITATION LIST

Patent Literature

PATENT LITERATURE 1: JP 2001-518320 T
PATENT LITERATURE 2. JP 2011-519632 T
PATENT LITERATURE 3: JP 2015-196092 A
PATENT LITERATURE 4: JP 2019-506230 T
PATENT LITERATURE 5: JP 2020-509922 T
PATENT LITERATURE 6: JP 2020-58808 A

SUMMARY OF INVENTION

Technical Problem

In the device as in Patent Literature 1 to 6, the opening through which a medical long object such as a coil can be inserted into the device is limited. Therefore, depending on the state of the lesion portion or the procedure, the medical long object may be difficult to be inserted into the device. In order to allow easy insertion of a medical long object into the device such as in Patent Literature 1 to 6, there is a problem that the size of the device itself becomes large. Thus, there has been room for improvement.

The present invention has been made in view of the circumstances above. An object of the present invention is to provide a medical device in which a medical long object is easily inserted inside a basket.

Solution to Problem

A medical device that has solved the above problems is as follows.

[1]A medical device comprising:

a basket having a plurality of wires;

a connection member disposed on a proximal side with respect to the basket; and a basket pusher disposed on the proximal side with respect to the connection member, wherein the connection member is capable of bending due to a weight of the basket, and an angle, measured under a condition below, on the proximal side between an extending direction of the basket pusher and a straight line passing through a distal end of the basket and a proximal end of the basket is 150 degrees or less,

[Condition]

in a state where, after the basket and the connection member have been immersed in 37° C. warm water for two minutes, a 0.1 g weight is connected, in 37° C. warm water, on a distal side with respect to a middle point of a length from the distal end of the basket to the proximal end of the basket, an angle on the proximal side between the extending direction of the basket pusher in a state where the basket pusher is horizontally fixed and the straight line passing through the distal end of the basket and the proximal end of the basket, is measured.

[2] The medical device according to [1], comprising an outer tube having a distal end and a proximal end, wherein the basket is disposed in an inner cavity of the outer tube and is expandable when having come out of the outer tube.

[3] The medical device according to [1] or [2], wherein the connection member is separable, and the basket is detachable from the basket pusher.

[4] The medical device according to any one of [1] to [3], wherein a length of the connection member in the extending direction of the basket pusher is shorter than a length of the basket pusher and a length of the basket, and a three-point bending stress of a material forming the connection member is lower than a three-point bending stress of a material forming the basket pusher and a three-point bending stress of a material forming the basket.

[5] The medical device according to any one of [1] to [4], wherein at a distal end of the basket pusher, the connection member is positioned inside the basket pusher, and in a dry state, an outer diameter of the connection member is smaller than an outer diameter of the distal end of the basket pusher and an outer diameter of the proximal end of the basket.

[6] The medical device according to any one of [1] to [4], wherein at a distal end of the basket pusher, the connection member is positioned outside the basket pusher, and in a dry state, an outer diameter of the connection member is larger than an outer diameter of the distal end of the basket pusher and is smaller than an outer diameter of the proximal end of the basket.

[7] The medical device according to any one of [1] to [6], wherein a material forming the connection member is a synthetic resin, and a material forming each of the basket pusher and the basket is a metal.

[8] The medical device according to any one of [1] to [7], wherein a material forming the connection member has a property of melting due to heat, and the medical device further comprises a heating mechanism configured to heat the connection member.

[9] The medical device according to any one of [1] to [8], wherein the basket includes a first bundling portion at which the plurality of wires are bundled and fixed at a distal portion of the basket, and a second bundling portion at which the plurality of wires are bundled and fixed at a proximal portion of the basket, in a cross-section perpendicular to the extending direction of the basket pusher, the connection member is disposed inside the second bundling portion, and the wires are disposed outside the connection member.

[10] The medical device according to [9], wherein the first bundling portion and the second bundling portion include a radiopaque material.

An aneurysm treatment method that has solved the above problems is as follows.

[11] An aneurysm treatment method using a medical device, the medical device including a basket having a plurality of wires, a connection member disposed on a proximal side with respect to the basket, and a basket pusher disposed on the proximal side with respect to the connection member, wherein the connection member is capable of bending due to a weight of the basket, and an angle, measured under a condition below, on the proximal side between an extending direction of the basket pusher and a straight line passing through a distal end of the basket and a proximal end of the basket is 150 degrees or less, the aneurysm treatment method comprising:

a step of inserting the basket into an artery and expanding the basket in an aneurysm of the artery; and a step of pushing the basket pusher in the extending direction thereof to cause an angle on the proximal side between the extending direction of the basket pusher and the straight line passing through the distal end of the basket and the proximal end of the basket, to be 150 degrees or less,

[Condition]

in a state where, after the basket and the connection member have been immersed in 37° C. warm water for two minutes, a 0.1 g weight is connected, in 37° C. warm water, on a distal side with respect to a middle point of a length from the distal end of the basket to the proximal end of the basket, an angle on the proximal side between the extending direction of the basket pusher in a state where the basket pusher is horizontally fixed and the straight line passing through the distal end of the basket and the proximal end of the basket, is measured.

[12] The aneurysm treatment method according to [11], comprising a step of disposing a medical long object into the basket.

Advantageous Effects of Invention

According to the medical device of the present invention, the connection member is capable of bending due to the weight of the basket, and in a state where, after the basket and the connection member have been immersed in 37° C. warm water for two minutes, a 0.1 g weight is connected, in 37° C. warm water, on the distal side with respect to the middle point of the length from the distal end of the basket to the proximal end of the basket, the angle on the proximal side between the extending direction of the basket pusher in a state where the basket pusher is horizontally fixed and the straight line passing through the distal end of the basket and the proximal end of the basket is 150 degrees or less. Therefore, a state where the basket is inclined with respect to the basket pusher can be established. Therefore, for example, in a state where the basket is indwelled inside a bulge after passing through the opening of the bulge, the side portion of the basket can be oriented toward the opening of the bulge. In the side portion of the basket, the gap between the plurality of wires of the basket is likely to become larger than in the proximal end portion and the distal end portion of the basket. Therefore, a medical long object such as a coil can be easily inserted in the inside of the basket through the gap between the plurality of wires.

BRIEF DESCRIPTION OF DRAWINGS

FIG. 1 shows a cross-sectional view, parallel to the extending direction of a basket pusher, of a distal end portion of a medical device in an embodiment of the present invention.

FIG. 2 shows a cross-sectional view, parallel to the extending direction of the basket pusher, showing a state where a basket is accommodated in an outer tube in the medical device shown in FIG. 1.

FIG. 3 shows an enlarged cross-sectional view, parallel to the extending direction of the basket pusher, of the part where a connection member of the medical device shown in FIG. 1 is present.

FIG. 4 shows an enlarged cross-sectional view, parallel to the extending direction of the basket pusher, of the part where the connection member of the medical device in another embodiment of the present invention is present.

FIG. 5 shows a V-V cross-sectional view of the medical device shown in FIG. 3.

FIG. 6 shows a VI-VI cross-sectional view of the medical device shown in FIG. 3.

FIG. 7 shows a VII-VII cross-sectional view of the medical device shown in FIG. 4.

DESCRIPTION OF EMBODIMENTS

Hereinafter, the present invention is specifically described below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

FIG. 1 is a cross-sectional view, parallel to the extending direction of a basket pusher 40, of a distal end portion of a medical device 1 in an embodiment of the present invention. In the present invention, the proximal side refers to the hand side of a user with respect to the extending direction of the basket pusher 40, and the distal side refers to the side opposite to the proximal side, i.e., the side (lesion portion side) where a treatment is performed by the medical device 1. The extending direction of the basket pusher 40 may be referred to as a longitudinal direction. In other words, the longitudinal direction of the basket pusher 40 is a distal-proximal direction of the basket pusher 40. In FIG. 1, the right side of the drawing is the proximal side and the left side of the drawing is the distal side. In FIG. 1, for easy understanding of the positional relationship between the respective members and sites, only some of a plurality of wires 20 of a basket 30 are shown, and the other wires are not shown.

As shown in FIG. 1, the medical device 1 of the present invention includes: the basket 30 having the plurality of wires 20; a connection member 80 disposed on the proximal side with respect to the basket 30; and the basket pusher 40 disposed on the proximal side with respect to the connection member 80. The connection member 80 is capable of bending due to the weight of the basket 30, and an angle θ1, measured under the condition below, on the proximal side between an extending direction L1 of the basket pusher 40 and a straight line L2 passing through a distal end 30*d* of the basket 30 and a proximal end 30*p* of the basket 30 is 150 degrees or less.

[Condition]

In a state where, after the basket 30 and the connection member 80 have been immersed in 37° C. warm water for two minutes, a 0.1 g weight is connected, in 37° C. warm water, on the distal side with respect to a middle point P1 of the length from the distal end 30*d* of the basket 30 to the proximal end 30*p* of the basket 30, the angle θ1 on the proximal side between the extending direction L1 of the basket pusher 40 in a state where the basket pusher 40 is horizontally fixed and the straight line L2 passing through the distal end 30*d* of the basket 30 and the proximal end 30*p* of the basket 30 is measured.

The medical device 1 can be used in, for example, embolization in which the basket 30 is indwelled in a vascular lesion portion such as an aneurysm to promote thrombosis to prevent rupture of the bulge. In embolization, for example, the basket 30 is disposed in a bulge in a terminal portion of an in-vivo lumen, a bulge in a side wall portion of an in-vivo lumen, a main tube peripheral portion of an in-vivo lumen, or the like. Then, a medical long object is indwelled inside the basket 30 disposed in the bulge, the main tube peripheral portion, or the like to promote thrombosis of the bulge. Examples of the medical long object include a coil, a wire, and a string-like object. Further, the medical long object may be a tube for transporting a long object such as a coil. In addition, the tubular medical long object may be for transporting a semi-solid fluid, a gel-like material, a semi-solid, a liquid, or the like, or further, a bag-like object, into a bulge. The liquid for the tubular medical long object may be a liquid that hardens or a liquid that is deposited, for example.

As shown in FIG. 1, the basket 30 has a plurality of wires 20. The basket 30 can be expanded and contracted. Specifically, when under an external force, the basket 30 is squeezed to enter a state of having a reduced diameter, and when not under an external force, the basket 30 is expanded to enter a state of having an enlarged diameter. When the basket 30 is disposed in a bulge, the basket 30 comes into contact with the bulge wall, to be subjected to an external force from the bulge and deformed.

The material forming each wire 20 preferably has elasticity, and examples thereof include metal wire materials that are single wires, flat wires, multi-wires, composite material wires, or twisted wires formed from stainless steel such as SUS304 and SUS316, platinum, nickel, cobalt, chromium, titanium, tungsten, aluminum, gold, silver, Ni—Ti alloys, Co—Cr alloys, etc. Among them, the material forming each wire 20 is preferably a material having superelasticity, and more preferably a metal wire material of a Ni—Ti alloy. When the material forming each wire 20 is a metal wire material of a Ni—Ti alloy, the elasticity of each wire 20 can be enhanced, and even if the deformation amount of the basket 30 released from the outer tube 10 is large, the return amount is large, and thus, the basket 30 can be less likely to lose its shape.

It is sufficient that the number of the wires 20 of the basket 30 is plural, and the number of the wires 20 can be selected according to the inner diameter of an in-vivo lumen or the like. In the drawings, the number of the wires 20 of the basket 30 is limited. However, in the embodiment of the present invention, the basket 30 can be, for example, a basket 30 including 8 or more and 64 or less wires 20. The diameter of each element wire of each wire 20 can be set according to the size of the basket 30, the number and the material of the wires 20, and the like. The number of the wires 20 of the basket 30 is preferably 16 or more and 32 or less.

As shown in FIG. 1, the connection member 80 is disposed on the proximal side with respect to the basket 30. The connection member 80 is a member that connects the basket 30 and the basket pusher 40 to each other. In other words, the basket 30 and the basket pusher 40 are connected directly or indirectly to each other via the connection member 80. Since the medical device 1 has the connection member 80 on the proximal side with respect to the basket 30 and on the distal side with respect to the basket pusher 40, connection between the basket 30 and the basket pusher 40 can be easily performed.

Preferably, the connection member 80 is severable. That is, preferably, the basket 30 can be detached from the basket pusher 40 by severing the connection member 80. In the case where the connection member 80 is severable, if the connection member 80 is severed after the basket 30 has been transported to a target site, the basket 30 is detached from the basket pusher 40, and thus, the basket 30 is easily indwelled in the target site.

As a method for severing the connection member 80, various methods such as a mechanical severing mechanism, fusion cutting, thermal, electrical, and chemical severing can used. Examples of the connection member 80 include rod-like objects, string-like objects, clips, members fitted to each other such as recesses and projections, etc. As the material forming the connection member 80, synthetic resins, metals, etc., can be used. The connection member 80 may be a member different from the basket 30 or the basket pusher 40, or may be a part of the basket 30 or the basket pusher 40.

As shown in FIG. 1, the basket pusher 40 is disposed on the proximal side with respect to the connection member 80. The basket pusher 40 is connected to the basket 30 via the connection member 80, and can move the basket 30 in the longitudinal direction of the outer tube 10, thereby releasing the basket 30 from the outer tube 10 or accommodating the basket 30 in the outer tube 10. Although not shown, the basket pusher 40 may include a handle for controlling the position in the longitudinal direction or rotation thereof, at a proximal end portion of the outer tube 10.

The material forming the basket pusher 40 is preferably a metal, and examples thereof include metals such as stainless steel, carbon steel, and nickel-titanium alloys. Among them, the material forming the basket pusher 40 is preferably stainless steel. When the material forming the basket pusher 40 is stainless steel, the rigidity of the basket pusher 40 can be enhanced. As a result, the force applied to the basket pusher 40 can be efficiently transmitted to the basket 30, and thus, it becomes easier to perform the operation of moving the basket 30 in the longitudinal direction.

As shown in FIG. 1, the connection member 80 is capable of bending due to the weight of the basket 30, and the angle θ1, measured under the condition below, on the proximal side between the extending direction L1 of the basket pusher 40 and the straight line L2 passing through the distal end 30*d* of the basket 30 and the proximal end 30*p* of the basket 30 is 150 degrees or less.

[Condition]

In a state where, after the basket 30 and the connection member 80 have been immersed in 37° C. warm water for two minutes, a 0.1 g weight is connected, in 37° C. warm water, on the distal side with respect to the middle point P1 of the length from the distal end 30*d* of the basket 30 to the proximal end 30*p* of the basket 30, the angle θ1 on the proximal side between the extending direction L1 of the basket pusher 40 in the state where the basket pusher 40 is horizontally fixed and the straight line L2 passing through the distal end 30*d* of the basket 30 and the proximal end 30*p* of the basket 30 is measured.

As shown in FIG. 1, when the distal end portion of the basket 30 has a recessed shape, the middle point of an imaginary straight line (indicated by a broken line in FIG. 1) connecting the parts positioned on the most distal side of at least two wires 20 of the basket 30 is assumed to be the distal end 30*d* of the basket 30.

Since the angle θ1 on the proximal side between the extending direction L1 of the basket pusher 40 and the straight line L2 passing through the distal end 30*d* of the basket 30 and the proximal end 30*p* of the basket 30 is 150 degrees or less, the connection member 80 can be flexible and bend, and thus, the basket 30 can be made into a state of being inclined with respect to the basket pusher 40. Therefore, for example, in the case where the basket 30 has been caused to pass through the opening of a bulge, to be indwelled inside the bulge, when the basket pusher 40 is pushed, the connection member 80 bends, whereby the distal end portion of the basket 30 is rotated and moved toward the proximal side. As a result, the side portion of the basket 30 can be oriented toward the opening of the bulge. In the side portion of the basket 30, the gap between the plurality of wires 20 of the basket 30 is likely to become larger than in the proximal end portion and the distal end portion of the basket 30. Therefore, a medical long object such as a coil can be easily inserted in the inside of the basket 30 through the gap between the plurality of wires 20.

The angle θ1 on the proximal side between the extending direction L1 of the basket pusher 40 and the straight line L2 passing through the distal end 30*d* of the basket 30 and the proximal end 30*p* of the basket 30 is 150 degrees or less. In particular, the angle θ1 on the proximal side between the extending direction L1 of the basket pusher 40 and the straight line L2 is preferably 145 degrees or less, more preferably 140 degrees or less, further preferably 135 degrees or less, still further preferably 130 degrees or less, particularly preferably 125 degrees or less, and most preferably 120 degrees or less. When the upper limit value of the angle θ1 is set to be in the above range, the basket 30 easily rotates on the side portion side with respect to the proximal end 30*p* of the basket 30, and a medical long object is easily inserted between the plurality of wires 20 of the basket 30.

The angle θ1 on the proximal side between the extending direction L1 of the basket pusher 40 and the straight line L2 passing through the distal end 30*d* of the basket 30 and the proximal end 30*p* of the basket 30 is preferably 70 degrees or more, more preferably 75 degrees or more, further preferably 80 degrees or more, still further preferably 85 degrees or more, and particularly preferably 90 degrees or more. When the lower limit value of the angle θ1 is set to be in the above range, the basket 30 easily rotates on the side portion side with respect to the distal end 30*d* of the basket 30, and a medical long object such as a coil can be easily inserted from the gap between the plurality of wires 20 of the basket 30.

In a state where, after the basket 30 and the connection member 80 have been immersed in 37° C. warm water for two minutes, a weight is connected, in 37° C. warm water, on the distal side with respect to the middle point P1 of the length from the distal end 30*d* of the basket 30 to the proximal end 30*p* of the basket 30, when the angle θ1 on the proximal side between the extending direction L1 of the basket pusher 40 in the state where the basket pusher 40 is horizontally fixed and the straight line L2 passing through the distal end 30*d* of the basket 30 and the proximal end 30*p* of the basket 30 is 150 degrees or less, the mass of the weight is preferably 0.1 g or less, more preferably 0.05 g or less, and further preferably 0.01 g or less. When the upper limit value of the mass of the weight with which the angle θ1 becomes 150 degrees or less is set to be in the above range, flexibility of the connection member 80 is enhanced, and the distal end portion of the basket 30 is easily rotated and moved toward the proximal side. The lower limit value of the mass of the weight with which the angle θ1 becomes 150 degrees or less is not limited in particular, and can be 0.001 g or more, for example.

The state where the angle θ1 on the proximal side between the extending direction L1 of the basket pusher 40 in the state where the basket pusher 40 is horizontally fixed and the straight line L2 passing through the distal end 30*d* of the basket 30 and the proximal end 30*p* of the basket 30 is 180 degrees is defined as, in terms of direction expression according to an analog clock, a state where the basket 30 is in the 12 o'clock direction with respect to the basket pusher 40. At this time, in a state where, after the basket 30 and the connection member 80 have been immersed in 37° C. warm water for two minutes, a 0.1 g weight is connected, in 37° C. warm water, on the distal side with respect to the middle point P1 of the length from the distal end 30*d* of the basket 30 to the proximal end 30*p* of the basket 30, the basket 30 is preferably in the direction of 8 o'clock to 10 o'clock with respect to the basket pusher 40. When the basket 30 is in the direction of 8 o'clock to 10 o'clock with respect to the basket pusher 40, the connection member 80 sufficiently and easily bends, and the basket 30 easily rotates on the side portion side with respect to the distal end 30*d* of the basket 30.

FIG. 2 is a cross-sectional view, parallel to the extending direction of the basket pusher 40, showing a state where the basket 30 is accommodated in the outer tube 10. In FIG. 2, the right side of the drawing is the proximal side and the left side of the drawing is the distal side.

Preferably, as shown in FIG. 2, the medical device 1 has the outer tube 10 having a distal end 10*d* and a proximal end 10*p*, and the basket 30 is disposed in the inner cavity of the outer tube 10 and is expandable when having come out of the outer tube 10. That is, preferably, the basket 30 is disposed in the lumen of the outer tube 10, and when released from the outer tube 10, the basket 30 becomes able to expand. When disposed in the inner cavity of the outer tube 10, the basket 30 is in contact with the inner wall of the outer tube 10, and is in a state of being squeezed and having a reduced diameter under an external force from the outer tube 10. When the basket 30 is released from the outer tube 10, the basket 30 is not subjected to the external force any more, and when no other external force is applied, the basket 30 enters a state of being expanded and having an enlarged diameter. Since the basket 30 is disposed in the inner cavity of the outer tube 10, the basket 30 is easily transported to a target site, and a procedure such as embolization using the medical device 1 is easily performed.

The outer tube 10 is a tubular member extending in the longitudinal direction and has at least one lumen extending in the longitudinal direction. The number of the lumens of the outer tube 10 may be plural, but is preferably one. When the number of the lumens of the outer tube 10 is one, the outer diameter of the outer tube 10 can be reduced. As a result, the minimal invasiveness of the medical device 1 can be improved.

The material forming the outer tube 10 is preferably a resin or a metal. Examples of the resin forming the outer tube 10 include polyamide-based resins, polyester-based resins, polyurethane-based resins, polyolefin-based resins, fluorine-based resins, vinyl chloride-based resins, silicone-based resins, natural rubber, etc. Only one of these materials may be used, or two or more of these materials may be used in combination. Among them, the resin forming the outer tube 10 is preferably at least one of polyamide-based resins, polyester-based resins, polyurethane-based resins, polyolefin-based resins, and fluorine-based resins. When the material forming the outer tube 10 is at least one of polyamide-based resins, polyester-based resins, polyurethane-based resins, polyolefin-based resins, and fluorine-based resins, the slipperiness of the surface of the outer tube 10 can be enhanced, and the insertability of the outer tube 10 into a lumen such as a blood vessel can be improved. A tube, to serve as the outer tube 10, that is formed from the resin can be produced by using a normal method such as extrusion molding and injection molding.

Examples of the metal forming the outer tube 10 include stainless steel such as SUS304 and SUS316, platinum, nickel, cobalt, chromium, titanium, tungsten, gold, Ni—Ti alloys, Co—Cr alloys, and combinations thereof. As a tube, to serve as the outer tube 10, that is formed from the metal, a tube obtained by spirally winding a metal wire material, a tube obtained by braiding metal wire materials, or the like may be used. In addition, the outer tube 10 may be a tube obtained by combining a metal and a resin. A tubular body formed from a resin and having a reinforcing material such as a metal wire material provided therein may be used as the outer tube 10. In the case where a tube-like member made of a resin and having a wire material provided therein is used as the outer tube 10, the wire material is preferably formed from a Ni—Ti alloy since the wire material has excellent shape memory properties and high elasticity. The wire material may be a fiber material of the above-described metal, a polyarylate fiber, an aramid fiber, an ultra-high molecular weight polyethylene fiber, a PBO fiber, a carbon fiber, or the like. The fiber material may be a monofilament or may be a multifilament.

The outer tube 10 may be composed of a single layer or may be composed of a plurality of layers. In addition, in the longitudinal direction, a part of the outer tube 10 may be composed of a single layer, and the other part of the outer tube 10 may be composed of a plurality of layers.

With respect to the outer tube 10, the outer surface of the outer tube 10 is preferably coated with a hydrophilic resin. That is, the outer tube 10 preferably has a hydrophilic resin layer outside the outer tube 10. When the outer surface of the outer tube 10 is coated with a hydrophilic resin, the slipperiness of the outer tube 10 can be enhanced, and insertability in an in-vivo lumen can be enhanced.

With respect to the outer tube 10, the inner surface of the outer tube 10 is preferably coated with a fluorine-based resin. In other words, the outer tube 10 preferably has a fluorine-based resin layer inside the outer tube 10. When the outer tube 10 has a fluorine-based resin layer inside the outer tube 10, the slipperiness of the inner surface the outer tube 10 is improved. Therefore, in the inner cavity of the outer tube 10, the basket 30 is easily moved in the longitudinal direction.

The cross-sectional shape of the outer shape of the outer tube 10 in a cross-section perpendicular to the longitudinal direction may be a circular shape, an elliptical shape, a polygonal shape, or a combination thereof. In addition, the cross-sectional shape of the inner cavity of the outer tube 10 in a cross-section perpendicular to the longitudinal direction may also be a circular shape, an elliptical shape, a polygonal shape, or a combination thereof.

Preferably, the basket 30 is slidable inside a tube having an inner diameter of 0.021 inches (0.5334 mm) or less. In the case where the number of the lumens of the outer tube 10 is one, preferably, the inner diameter of the outer tube 10 is 0.021 inches or less, and the basket 30 is disposed in the inner cavity of this outer tube 10. In the case where the outer tube 10 has a plurality of lumens, the inner diameter of the lumen in which the basket 30 is disposed is preferably 0.021 inches or less. When the basket 30 is slidable inside a tube having an inner diameter of 0.021 inches or less, the outer diameter of the outer tube 10 can be reduced. Accordingly, the medical device 1 that has good insertability and that is minimally invasive can be realized.

Preferably, the connection member 80 is separable, and the basket 30 is detachable from the basket pusher 40. That is, preferably, the basket 30 is detachable from the basket pusher 40 by separating the connection member 80. In the case where the connection member 80 is separable, if the connection member 80 is separated after the basket 30 has been transported to a target site, the basket 30 is detached from the basket pusher 40, and thus, the basket 30 is easily indwelled in the target site.

As a method for separating the connection member 80, various methods such as a mechanical severing mechanism, fusion cutting, and thermal, electrical, and chemical severing can be used.

Preferably, as shown in FIG. 2, the length of the connection member 80 in the extending direction of the basket pusher 40 is shorter than the length of the basket pusher 40 and the length of the basket 30. Preferably, the three-point bending stress of the material forming the connection member 80 is lower than the three-point bending stress of the material forming the basket pusher 40 and the three-point bending stress of the material forming the basket 30. That is, preferably, the material forming the connection member 80 has a three-point bending stress lower than those of both of the material forming the basket pusher 40 and the material forming the basket 30. When the length of the connection member 80 in the extending direction of the basket pusher 40 is shorter than the length of the basket pusher 40 and the length of the basket 30, and the three-point bending stress of the material forming the connection member 80 is lower than the three-point bending stress of the material forming the basket pusher 40 and the three-point bending stress of the material forming the basket 30, the connection member 80 becomes flexible as compared with the basket pusher 40 and the basket 30. Therefore, the connection member 80 easily bends due to the weight of the basket 30.

The three-point bending stress is a bending stress determined by a three-point bending test performed on a test piece. The bending stress can be determined by the formula below.

$$\sigma = M/Z = (8\ PL)/(\pi d3)$$

σ: bending stress
M: (PL)/4: moment
Z: (2I)/D: section modulus
I: moment of inertia of area
When the test piece is a round bar, I: (πD4)/64
When the test piece is a round tube bar, I: (π/64)×(D4/d4)
D: outer diameter of test piece
d: diameter of inner cavity of test piece
P: bending load
L: distance between fulcrums The length of the connection member 80 in the extending direction of the basket pusher 40 is preferably 50% or less, more preferably 40% or less, and further preferably 30% or less of the length of the basket 30. When the upper limit value of the ratio between the length of the connection member 80 and the length of the basket 30 is set to be in the above range, the connection member 80 has sufficient strength, and the force that pushes and moves the basket pusher 40 to the distal side is easily transmitted to the basket 30. The length of the connection member 80 in the extending direction of the basket pusher 40 is preferably 5% or more, more preferably 7% or more, and further preferably 10% or more of the length of the basket 30. When the lower limit value of the ratio between the length of the connection member 80 and the length of the basket 30 is set to be in the above range, the flexibility of the connection member 80 is enhanced and the connection member 80 easily bends.

FIG. 3 is an enlarged cross-sectional view, parallel to the extending direction of the basket pusher 40, of the part where the connection member 80 of the medical device 1 is present in the embodiment of the present invention. FIG. 5 is a cross-sectional view, perpendicular to the extending direction of the basket pusher 40, at a second bundling portion 52 of the medical device 1. FIG. 6 is a cross-sectional view, perpendicular to the extending direction of the basket pusher 40, of the part where the connection member 80 is present inside the basket pusher 40 of the medical device 1. In FIG. 3, the right side of the drawing is the proximal side and the left side of the drawing is the distal side. In FIG. 3, for easy understanding of the positional relationship between the respective members and sites, only some of the plurality of wires 20 of the basket 30 are shown, and the other wires are not shown.

Preferably, as shown in FIG. 3, FIG. 5, and FIG. 6, at a distal end 40*d* of the basket pusher 40, the connection member 80 is positioned inside the basket pusher 40, and in a dry state, the outer diameter of the connection member 80 is smaller than the outer diameter of the distal end 40*d* of the basket pusher 40 and the outer diameter of the proximal end 30*p* of the basket 30. That is, preferably, a proximal end 80*p* of the connection member 80 is positioned inside the basket pusher 40 and a distal end 80*d* of the connection member 80 is positioned inside the basket 30. When the proximal end 80*p* of the connection member 80 is positioned inside the basket pusher 40 and the distal end 80*d* of the connection member 80 is positioned inside the basket 30, the proximal end portion including the proximal end 80*p* of the connection member 80 is protected by the basket pusher 40 and the distal end portion including the distal end 80*d* of the connection member 80 is protected by the basket 30. Therefore, unintentional detachment of the connection member 80 from the basket pusher 40 or the basket 30 is less likely to occur.

FIG. 4 is an enlarged cross-sectional view, parallel to the extending direction of the basket pusher 40, of the part where the connection member 80 of the medical device 1 is present in another embodiment of the present invention. FIG. 7 is a cross-sectional view, perpendicular to the extending direction of the basket pusher 40, of the part where the basket pusher 40 is present inside the connection member 80 of the medical device 1. In FIG. 4, the right side of the drawing is the proximal side and the left side of the drawing is the distal side. In FIG. 4, for easy understanding of the positional relationship between the respective members and sites, only some of the plurality of wires 20 of the basket 30 are shown, and the other wires are not shown.

In addition, preferably, as shown in FIG. 4 and FIG. 7, at the distal end 40*d* of the basket pusher 40, the connection member 80 is positioned outside the basket pusher 40, and in a dry state, the outer diameter of the connection member 80 is larger than the outer diameter of the distal end 40*d* of the basket pusher 40 and smaller than the proximal end 30*p* of the basket 30. That is, preferably, the distal end 40*d* of the basket pusher 40 is positioned inside the connection member 80, and the distal end 80*d* of the connection member 80 is positioned inside the basket 30. When the distal end 40*d* of the basket pusher 40 is positioned inside the connection member 80, the distal end portion including the distal end 40*d* of the basket pusher 40 is present inside the connection member 80, whereby the rigidity in the vicinity of the proximal end 80*p* of the connection member 80 in the dry state is enhanced. Therefore, the force to push the basket pusher 40 from the hand side toward the distal side for transportation of the basket 30 is easily transmitted to the basket 30 via the connection member 80, and pushability of the medical device 1 can be enhanced. Further, when the distal end 80*d* of the connection member 80 is positioned inside the basket 30, the distal end portion including the distal end 80*d* of the connection member 80 is protected by the basket 30. Accordingly, the connection member 80 can be less likely to be detached from the basket 30.

Preferably, the material forming the connection member 80 is a synthetic resin, and the material forming each of the basket pusher 40 and the basket 30 is a metal. When the material forming the connection member 80 is a synthetic resin and the material forming each of the basket pusher 40 and the material forming the basket 30 is a metal, the connection member 80 can be flexible as compared with the basket pusher 40 and the basket 30, and the connection member 80 easily bends due to the weight of the basket 30.

Preferably, the material forming the connection member 80 has a property of melting due to heat, and the medical device 1 has a heating mechanism 90 for heating the connection member 80. When the material forming the connection member 80 has a property of melting due to heat and the medical device 1 has the heating mechanism 90, the connection member 80 can be melted and broken by the heating mechanism 90 heating the connection member 80, whereby the basket 30 can be detached from the basket pusher 40. Therefore, the basket 30 and the basket pusher 40 can be firmly connected by the connection member 80 until the heating mechanism 90 is activated, and the connection member 80 can be easily severed when the heating mechanism 90 is activated. Thus, the basket 30 can be easily and reliably indwelled.

As the material forming the connection member 80 and having a property of melting due to heat, thermoplastic resins are preferable, and among them, PVA (polyvinyl alcohol) is more preferable. When the material forming the connection member 80 is PVA, the connection member 80 can be more easily severed, and thus, the medical device 1 that is easily handled can be realized.

Preferably, the heating mechanism 90 is connected to the basket pusher 40. When the heating mechanism 90 is connected to the basket pusher 40, the connection member 80 can be heated via the basket pusher 40, and thus, it is not necessary to additionally provide a member for transmitting the heat of the heating mechanism 90 to the connection member 80. Accordingly, the size of the medical device 1 can be reduced.

Preferably, as shown in FIG. 1 and FIG. 2, the basket 30 includes a first bundling portion 51 at which the plurality of wires 20 are bundled and fixed at a distal portion of the basket 30, and the second bundling portion 52 at which the plurality of wires 20 are bundled and fixed at a proximal portion of the basket 30, and as shown in FIG. 5, in a cross-section perpendicular to the extending direction of the basket pusher 40, the connection member 80 is disposed inside the second bundling portion 52, and the wires 20 are disposed outside the connection member 80. When the connection member 80 is disposed inside the second bundling portion 52 and the wires 20 are disposed outside the connection member 80, connection strength between the connection member 80 and the basket 30 can be enhanced, and unintentional detachment of the basket 30 can be prevented.

Preferably, the basket 30 is formed, between the first bundling portion 51 and the second bundling portion 52, in a cage shape obtained by braiding a plurality of wires 20 having been bent or right-handed and left-handed spiral wires 20, for example. Among them, the basket 30 is preferably formed by braiding right-handed spiral wires 20 and left-handed spiral wires 20. When right-handed spiral wires 20 and left-handed spiral wires 20 are braided to form the basket 30, the basket 30 can have a cage shape having a mesh-like wall surface. As a result, an object contained inside the basket 30 is less likely to get out of the basket 30, whereby promotion of thrombosis can be easily and efficiently performed.

Examples of a method for bundling and fixing the plurality of wires 20 at the first bundling portion 51 and the second bundling portion 52 include welding the plurality of wires 20, crimping the plurality of wires 20 together using a separate member, adhering the plurality of wires 20 using an adhesive, and fixing the plurality of wires 20 with a brazing material, and a combination thereof. Among them, crimping and fixing the plurality of wires 20 by the separate member at the first bundling portion 51 and the second bundling portion 52 is preferable. When the plurality of wires 20 are crimped and fixed by the separate member at the first bundling portion 51 and the second bundling portion 52, the plurality of wires 20 are easily and firmly fixed at the first bundling portion 51 and the second bundling portion 52, and the basket 30 is less likely to be broken.

Examples of the separate member that bundles and fixes the plurality of wires 20 at the first bundling portion 51 and the second bundling portion 52 include a ring-shaped member, a member having a C-shaped cross-section obtained by making a cut in a ring, a coil-shaped member obtained by winding a wire material, and a member that binds and fixes the plurality of wires 20 with a string-like object. Among them, the separate member that bundles and fixes the plurality of wires 20 is preferably a ring-shaped member, and more preferably a ring-shaped swaged member. When the separate member that bundles and fixes the plurality of wires 20 is a ring-shaped swaged member, the plurality of wires 20 can be firmly fixed, and the plurality of wires 20 can be less likely to be de-bundled.

As the material forming the separate member that bundles and fixes the plurality of wires 20, the same materials as those for the wires 20 of the basket 30 and the basket pusher 40 can be used, for example. Among them, the material forming the separate member that bundles and fixes the plurality of wires 20 is preferably stainless steel. When the material forming the separate member that bundles and fixes the plurality of wires 20 is stainless steel, the fixing strength of the plurality of wires 20 can be enhanced, and the durability of the separate member that bundles and fixes the plurality of wires 20 can be improved. Further, the material forming the separate member that bundles and fixes the plurality of wires 20 is more preferably a radiopaque material. Examples of the radiopaque material include platinum, gold, tungsten, iridium, palladium, tantalum, and an alloy in which at least one of these is combined. When the material forming the separate member that bundles and fixes the plurality of wires 20 is the radiopaque material, the positions of the first bundling portion 51 and the second bundling portion 52 can be confirmed under X-ray fluoroscopy. Thus, it is possible to grasp the position of the basket 30 in a body.

Preferably, as shown in FIG. 2, in the state where the basket 30 is accommodated in the outer tube 10, the first bundling portion 51 is positioned on the distal side with respect to a distal end 20*d* of the wires 20. The first bundling portion 51 is the part where the plurality of wires 20 of the basket 30 are bundled and fixed. In the state where the basket 30 is accommodated in the outer tube 10, when the first bundling portion 51 is positioned on the distal side with respect to the distal end 20*d* of the wires 20, the plurality of wires 20 bundled at the first bundling portion 51 are less likely to be de-bundled. Therefore, the basket 30 can be easily released from the outer tube 10 in a state where the respective plurality of wires 20 maintain their phases.

Preferably, as shown in FIG. 2, the second bundling portion 52 is positioned on the proximal side with respect to a proximal end 20*p* of each wire 20. Similar to the first bundling portion 51, the second bundling portion 52 is the part where the plurality of wires 20 of the basket 30 are bundled and fixed, and thus, the rigidity tends to be higher than the other part of the basket 30. When the second bundling portion 52 is positioned on the proximal side with respect to the proximal end 20*p* of each wire 20, the rigidity of the proximal end portion of the basket 30 can be enhanced, and the force applied from the hand side to push the basket 30 to the distal side can be efficiently transmitted to the basket 30. As a result, the medical device 1 in which the basket 30 is easily released from the outer tube 10 can be realized.

Preferably, the first bundling portion 51 and the second bundling portion 52 include a radiopaque material. When the first bundling portion 51 and the second bundling portion 52 include the radiopaque material, the positions of the first bundling portion 51 and the second bundling portion 52 can be confirmed under X-ray fluoroscopy. As a result, the position of the basket 30 in a body can be grasped.

Examples of the radiopaque material include platinum, gold, tungsten, iridium, palladium, tantalum, and an alloy in which at least one of these is combined.

Each wire 20 of the basket 30 preferably includes a superelastic alloy. When each wire 20 includes a superelastic alloy, the basket 30 becomes excellent in elasticity. When the basket 30 is excellent in elasticity, the deformation amount of the basket 30 can be made large. Therefore, the basket 30 can be accommodated in the outer tube 10 having a small outer diameter, and the basket 30 can be expanded to a large extent when the basket 30 comes out of the outer tube 10.

Preferably, each wire 20 of the basket 30 includes the radiopaque material. When each wire 20 includes the radiopaque material, the position and the state of the expansion of the basket 30 can be confirmed under X-ray fluoroscopy, and the procedure is easily and smoothly performed.

Next, an aneurysm treatment method of the present invention will be described. In the following descriptions, the same descriptions as the above descriptions will be omitted.

The aneurysm treatment method of the present invention is an aneurysm treatment method that uses the medical device 1 of the present invention. The aneurysm treatment method includes: a step of inserting the basket 30 into an artery and expanding the basket 30 in an aneurysm of the artery; and a step of pushing the basket pusher 40 in the extending direction thereof to cause the angle θ1 on the proximal side between the extending direction L1 of the basket pusher 40 and the straight line L2 passing through the distal end 30*d* of the basket 30 and the proximal end 30*p* of the basket 30, to be 150 degrees or less.

In aneurysm treatment according to the present invention, the medical device 1 that has the basket 30 having a plurality of wires 20, the connection member 80 disposed on the proximal side with respect to the basket 30, and the basket pusher 40 disposed on the proximal side with respect to the connection member 80, wherein the connection member 80 is capable of bending due to the weight of the basket 30, is used. That is, in the aneurysm treatment method of the present invention, the medical device 1 of the present invention described above is used.

In the step of inserting the basket 30 having the plurality of wires 20 into an artery and expanding the basket 30 in an aneurysm of the artery, specifically, the basket 30 is inserted in the artery having the aneurysm, the basket 30 is transported through the opening of the aneurysm to the inside of the aneurysm, and the basket 30 is expanded in the aneurysm.

In the step of pushing the basket pusher 40 in the extending direction thereof to cause the angle θ1 on the proximal side between the extending direction L1 of the basket pusher 40 and the straight line L2 passing through the distal end 30*d* of the basket 30 and the proximal end 30*p* of the basket 30, to be 150 degrees or less, the basket pusher 40 is pushed in the extending direction to change the orientation of the basket 30 expanded in the aneurysm. Specifically, for example, the basket pusher 40 is pushed from the hand side toward the distal side, and the basket 30 is pushed in the aneurysm along the bulge wall by the basket pusher 40, whereby the basket 30 is rotated, and the orientation of the basket 30 is changed. As a result, the position of the distal end portion or the proximal end portion of the basket 30 where the density of the plurality of wires 20 forming the basket 30 is high can be changed, the basket 30 is easily brought into close contact with the aneurysm, and treatment of the aneurysm can be easily performed.

In the step of rotating the basket 30 in the aneurysm, the rotation angle of the basket 30 is 150 degrees or less. That is, the angle θ1 on the proximal side between the extending direction L1 of the basket pusher 40 and the straight line L2 passing through the distal end 30*d* of the basket 30 and the proximal end 30*p* of the basket 30 is 150 degrees or less. Since the rotation angle of the basket 30 is 150 degrees or less, the basket 30 can be sufficiently rotated in the aneurysm.

Further preferably, a step of disposing a medical long object into the basket 30 is included. When the basket 30 is rotated in the aneurysm, the side portion of the basket 30 where the gap between the plurality of wires 20 forming the basket 30 tends to be more largely open than at the distal end portion or the proximal end portion of the basket 30 is oriented toward the opening of the aneurysm. Therefore, in embolization, which is an aneurysm treatment method, a medical long object such as a coil can be easily disposed inside the basket 30, whereby treatment of the aneurysm can be smoothly performed.

As described above, the medical device of the present invention includes: a basket having a plurality of wires; a connection member disposed on the proximal side with respect to the basket; and a basket pusher disposed on the proximal side with respect to the connection member. The connection member is capable of bending due to the weight of the basket. In a state where, after the basket and the connection member have been immersed in 37° C. warm water for two minutes, a 0.1 g weight is connected, in 37° C. warm water, on the distal side with respect to the middle point of the length from the distal end of the basket to the proximal end of the basket, the angle on the proximal side between the extending direction of the basket pusher in a state where the basket pusher is horizontally fixed and a straight line passing through the distal end of the basket and the proximal end of the basket is 150 degrees or less. Since the medical device of the present invention has such a configuration, a state where the basket is inclined with respect to the basket pusher can be established. Therefore, for example, in a state where the basket is indwelled inside a bulge after passing through the opening of the bulge, the side portion of the basket can be oriented toward the opening of the bulge. In the side portion of the basket, the gap between the plurality of wires of the basket is likely to become larger than in the proximal end portion and the distal end portion of the basket. Therefore, a medical long object such as a coil can be easily inserted in the inside of the basket through the gap between the plurality of wires.

This application claims priority to Japanese Patent Application No. 2022-053544, filed on Mar. 29, 2022. All of the contents of the Japanese Patent Application No. 2022-053544, filed on Mar. 29, 2022, are incorporated by reference herein.

REFERENCE SIGNS LIST

1: medical device
10: outer tube
10*d*: distal end of the outer tube
10*p*: proximal end of the outer tube
20: wire
20*d*: distal end of the wire
20*p*: proximal end of the wire
30: basket
30*d*: distal end of the basket
30*p*: proximal end of the basket
40: basket pusher
40*d*: distal end of the basket pusher
51: first bundling portion
52: second bundling portion
80: connection member
80*d*: distal end of the connection member
80*p*: proximal end of the connection member
90: heating mechanism
L1: extending direction of the basket pusher
L2: straight line passing through the distal end of the basket and the proximal end of the basket
θ1: angle on the proximal side between the extending direction of the basket pusher and the straight line passing through the distal end of the basket and the proximal end of the basket
P1: middle point of the length from the distal end of the basket to the proximal end of the basket

The invention claimed is:

1. A medical device comprising:
a basket having a plurality of wires;
a connection member disposed on a proximal side with respect to, and directly connected to, the basket; and
a basket pusher directly connected to a proximal side of the connection member, so that the basket is connected to the basket pusher via the connection member, wherein the connection member is more flexible than the basket,
the connection member being a material having a property of melting due to heat, and
the material of the connection member having a property of bending due to a weight of the basket, and an angle, measured under a condition below, on the proximal side between an extending direction of the basket pusher and a straight line passing through a distal end of the basket and a proximal end of the basket is 150 degrees or less,
[Condition]
in a state where, after the basket and the connection member have been immersed in 37° C. warm water for two minutes, a 0.1 g weight is connected, in the 37° C. warm water, on a distal side with respect to a middle point of a length from the distal end of the basket to the proximal end of the basket, an angle on the proximal side between the extending direction of the basket pusher in a state where the basket pusher is horizontally fixed and the straight line passing through the distal end of the basket and the proximal end of the basket, is measured.

2. The medical device according to claim 1, further comprising an outer tube having a distal end and a proximal end, wherein
the basket is disposed in an inner cavity of the outer tube and is expandable when having come out of the outer tube.

3. The medical device according to claim 1, wherein
the connection member is configured to be separable so that the basket is detachable from the basket pusher.

4. The medical device according to claim 1, wherein
a length of the connection member in the extending direction of the basket pusher is shorter than a length of the basket pusher and a length of the basket, and
a three-point bending stress of a material forming the connection member is lower than a three-point bending stress of a material forming the basket pusher and a three-point bending stress of a material forming the basket.

5. The medical device according to claim 1, wherein at a distal end of the basket pusher, the connection member is positioned inside the basket pusher, and in a dry state, an outer diameter of the connection member is smaller than an outer diameter of the distal end of the basket pusher and an outer diameter of the proximal end of the basket.

6. The medical device according to claim 1, wherein at a distal end of the basket pusher, the basket pusher is positioned inside the connection member, and in a dry state, an outer diameter of the connection member is larger than an outer diameter of the distal end of the basket pusher and is smaller than an outer diameter of the proximal end of the basket.

7. The medical device according to claim 1, wherein a material forming the connection member is a synthetic resin, and a material forming each of the basket pusher and the basket is a metal.

8. The medical device according to claim 1, wherein the medical device further comprises a heater configured to heat the connection member so that the basket is detachable from the basket pusher.

9. The medical device according to claim 1, wherein the basket includes a first bundling portion at which the plurality of wires are bundled and fixed at a distal portion of the basket, and a second bundling portion at which the plurality of wires are bundled and fixed at a proximal portion of the basket, in a cross-section perpendicular to the extending direction of the basket pusher, the connection member is disposed inside the second bundling portion, and the wires are disposed outside the connection member.

10. The medical device according to claim 9, wherein the first bundling portion and the second bundling portion include a radiopaque material.

11. An aneurysm treatment method using the medical device of claim 1, the aneurysm treatment method comprising:

a step of inserting the basket into an artery and expanding the basket in an aneurysm of the artery; and a step of pushing the basket pusher in the extending direction thereof to cause an angle on the proximal side between the extending direction of the basket pusher and the straight line passing through the distal end of the basket and the proximal end of the basket, to be 150 degrees or less.

12. The aneurysm treatment method according to claim 11, further comprising a step of disposing a medical long object into the basket.

13. The aneurysm treatment method according to claim 12, wherein in the step of disposing the medical long object into the basket, the medical long object is introduced into an interior of the basket through a gap between wires forming a mesh wall surface of the basket.

14. The medical device according to claim 1, wherein the basket is configured to receive a medical long object inside the basket.

15. The medical device according to claim 1, wherein the material of the connection member is polyvinyl alcohol.

* * * * *